United States Patent
Shaffer

(10) Patent No.: US 10,062,261 B2
(45) Date of Patent: Aug. 28, 2018

(54) WATER HEATER ODOR PRECURSOR DETECTION SYSTEM AND METHOD

(71) Applicant: Haier US Appliance Solutions, Inc., Wilmington, DE (US)

(72) Inventor: Timothy Scott Shaffer, La Grange, KY (US)

(73) Assignee: Haier US Appliance Solutions, Inc., Wilmington, DE (US)

(*) Notice: Subject to any disclaimer, the term of this patent is extended or adjusted under 35 U.S.C. 154(b) by 55 days.

(21) Appl. No.: 15/246,611

(22) Filed: Aug. 25, 2016

(65) Prior Publication Data

US 2018/0061205 A1    Mar. 1, 2018

(51) Int. Cl.
| | |
|---|---|
| G08B 21/18 | (2006.01) |
| G01N 33/18 | (2006.01) |
| G08B 7/06 | (2006.01) |
| G08B 3/10 | (2006.01) |
| G08B 5/36 | (2006.01) |

(52) U.S. Cl.
CPC ....... G08B 21/182 (2013.01); G01N 33/1886 (2013.01); G08B 3/10 (2013.01); G08B 5/36 (2013.01); G08B 7/06 (2013.01)

(58) Field of Classification Search
CPC ...... C02F 2303/02; F24H 1/18; F24H 9/0005; F24H 1/202; G01C 9/34; F24D 19/0092; F24D 2220/042; F24D 17/0073; F28F 19/00; G01N 27/62; G01N 27/622; A61M 35/003
See application file for complete search history.

(56) References Cited

U.S. PATENT DOCUMENTS

| | | | |
|---|---|---|---|
| 5,808,277 A * | 9/1998 | Dosani | F24D 17/0073 219/481 |
| 6,808,639 B2 | 10/2004 | Rawson et al. | |
| 2004/0112844 A1* | 6/2004 | Rawson | C02F 1/74 210/758 |
| 2010/0219082 A1* | 9/2010 | Diaz Gonzalez Alcocer | C02F 1/5245 205/743 |
| 2010/0308995 A1* | 12/2010 | Goto | G08B 1/00 340/540 |
| 2014/0284479 A1* | 9/2014 | Sato | G01N 27/62 250/336.1 |

FOREIGN PATENT DOCUMENTS

| | | |
|---|---|---|
| CN | 104807194 A | 7/2015 |
| JP | 2009024960 A | 2/2009 |

* cited by examiner

*Primary Examiner* — Mirza Alam
(74) *Attorney, Agent, or Firm* — Dority & Manning, P.A.

(57) ABSTRACT

A system and related methods for detecting precursors prior to the formation of odor-causing compounds in a water heater appliance. A sulfate probe including a sulfate-selective electrode is in operative communication with a voltage sensor sensing open circuit potential between the water heater tank and the sulfate sensor probe. A method of alerting a consumer includes monitoring open circuit potential between a water heater tank and a sulfate sensor probe, evaluating the open circuit potential to determine a concentration of an odor precursor, and issuing an alert when the odor precursor concentration reaches a predetermined amount.

14 Claims, 5 Drawing Sheets

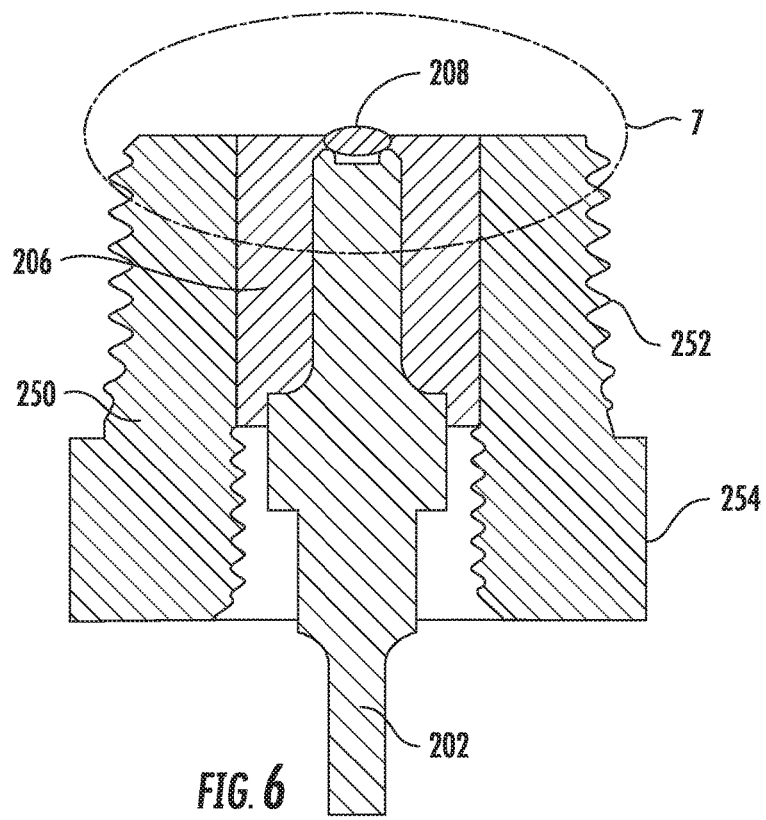
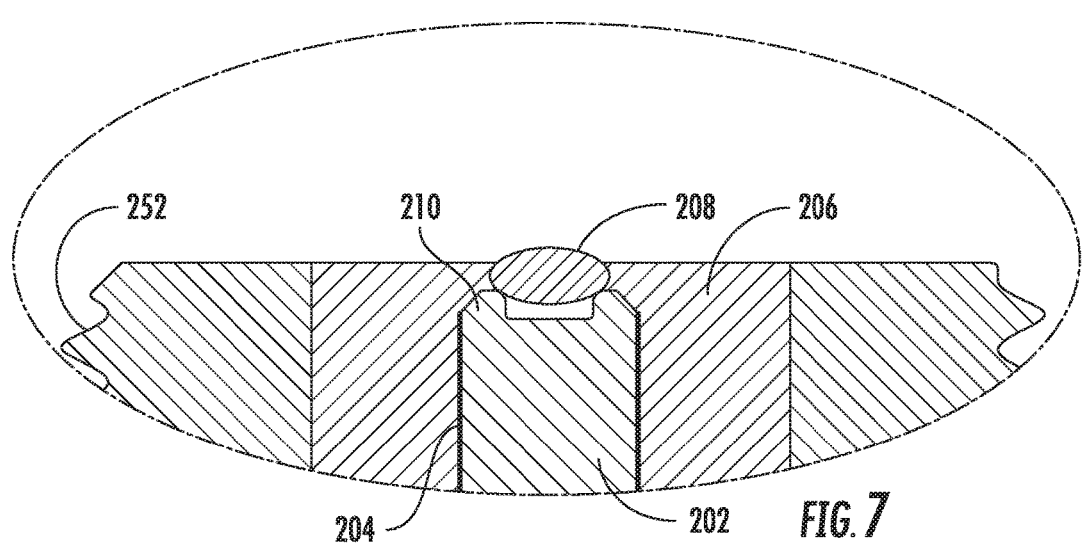

WATER HEATER ODOR PRECURSOR DETECTION SYSTEM AND METHOD

FIELD OF THE INVENTION

The present subject matter relates generally to water heater appliances, and more particularly to a system and method for detecting odor precursors in water heater appliances.

BACKGROUND OF THE INVENTION

The quality of a water supply can vary between sources and even from time to time within the same source. Certain substances can have negative effects when present in sufficient quantity in a user's water system. For example, hydrogen sulfide ($H_2S$) is a notorious chemical, being widely known and well-recognized by smell, if not always by name. The characteristic "rotten egg" odor of $H_2S$ is almost universally reviled. Thus, the presence of a significant quantity of $H_2S$, i.e., enough to be readily detected by ordinary olfactory perception, within a building, and in particular a residence, is undesired.

However, when conditions are favorable, $H_2S$ may be spontaneously generated in a water heater appliance. For example, $H_2S$ may be generated from reduction of sulfate ($SO_4$) ions. As such, a sufficient amount of $SO_4$, which can be naturally-occurring in a water supply, along with sulfate reducing bacteria and/or necessary thermochemical conditions, may eventually create a bad smelling/tasting condition from the water heater in the user's home. Therefore, because sulfate is a precursor to odiferous $H_2S$, there is a need to identify when naturally-occurring sulfates are present in the water heater tank such that the user can be alerted and then can take proactive steps to prevent $H_2S$ generation.

Electrochemical sensors which detect sulfide are generally known. However, such electrochemical sulfide sensors are limited in their operating range in that they require very basic (e.g., pH>11) conditions and are therefore generally not usable in residential water heaters. Also, earlier detection of a potential problem, e.g., by detecting precursors rather than the malodorous compound itself, is more desirable.

Accordingly, a water heater appliance with features for detecting precursors prior to the formation of odor-causing compounds would be useful.

BRIEF DESCRIPTION OF THE INVENTION

The present subject matter provides an improved water heater appliance with a sulfate sensor and methods of alerting a consumer upon detection of sulfates. Additional aspects and advantages of the invention will be set forth in part in the following description, or may be apparent from the description, or may be learned through practice of the invention.

In a first exemplary embodiment, a water heater odor precursor detection system is provided. The water heater odor precursor detection system includes a water heater tank, a sulfate sensor probe mounted to the water heater tank and a voltage sensor circuit in operative communication with the water heater tank and the sulfate sensor probe. The voltage sensor circuit is operable to sense an open circuit potential between the water heater tank and the sulfate sensor probe. The water heater odor precursor detection system also includes a controller configured to receive a signal from the voltage sensor circuit, the signal indicative of the sensed open circuit potential. The controller is configured to provide an output signal based on the signal, and an indicator is configured to provide an indication of odor precursor detection based on said output signal.

In a second exemplary embodiment, a method of alerting a consumer upon detection of an odor precursor in a water heater is provided. The method includes monitoring open circuit potential between a water heater tank and a sulfate sensor probe, evaluating the open circuit potential to determine the concentration of an odor precursor, and issuing an alert when odor precursor concentration reaches a predetermined amount.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

FIG. 6 provides a section view of a sulfate sensor probe according to an exemplary embodiment of the present subject matter;

FIG. 7 provides an enlarged view of the exemplary probe of FIG. 6; and

DETAILED DESCRIPTION

Figure 1:
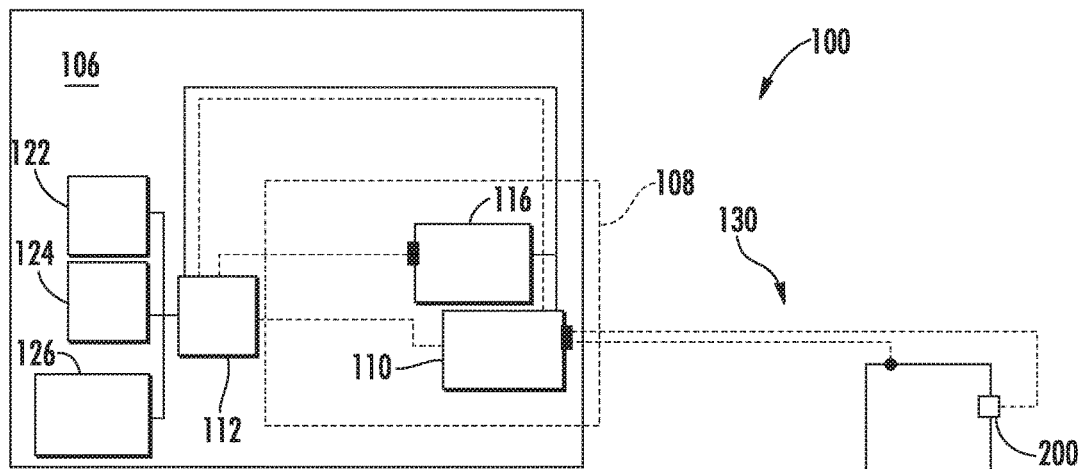
FIG. 1 provides a block diagram of an odor precursor detection system according to an exemplary embodiment of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 1A:
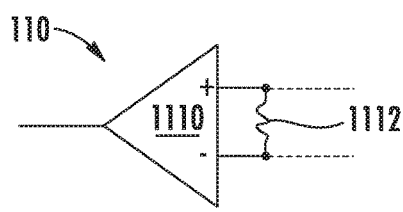
FIG. 1A illustrates an exemplary operational amplifier and shunt resistor circuit usable with the exemplary system of FIG. 1.

FIG. 1 illustrates an exemplary odor precursor detection system 100 according to the present subject matter in the form of a block diagram. Odor precursor detection system 100 comprises two major components, an open circuit 130 and an electronic control board 106. The open circuit 130 includes a tank 102 of a water heater 104 together with a sulfate sensor probe 200 mounted to tank 102. Electronic control board 106 includes, among other sub-components, voltage sensor circuit 108. Voltage sensor circuit 108 includes a resistor 1112 as illustrated in FIG. 1A as part of operational amplifier (op-amp) circuit 110. In some exemplary embodiments, resistor 1112 can be a shunt resistor. Op-amp circuit 110 may further include op-amp 1110, e.g., as illustrated in FIG. 1A. In some exemplary embodiments, op-amp 1110 can be a differential op-amp.

In accordance with the present subject matter, the electronic control board 106 comprises microcontroller 112, power supply 116, op-amp circuit 110, and various connections to the tank 102 and probe 200. Microcontroller 112 receives inputs from operational amplifier 110. It should be appreciated that microcontroller 112 may correspond to other types of controllers including a microprocessor or other specially designed hardware and thus the designation as a microcontroller is used broadly herein. Microcontroller 112 can be configured to evaluate the sensed open circuit potential, such as by comparing the sensed open circuit potential to a predetermined correlation between the open circuit potential and a sulfate concentration value. Microcontroller 112 can further be configured to provide user feedback by way of one or more of a User Interface (UI) display 122, UI sound producing device 124, or by way of connected home appliance communication by network connection 126, especially to provide an alert when the sulfate concentration value is above a predetermined threshold amount. The sulfate sensor probe 200 may be able to detect sulfate concentrations in parts per million (ppm) ranging from about one-tenth (0.1 ppm) to about one thousand (1,000 ppm). In some exemplary embodiments, the predetermined threshold amount triggering a user alert may be between one part sulfate per million parts water (1 ppm of $SO_4$) and one hundred parts sulfate per million parts water (100 ppm of $SO_4$). In some exemplary embodiments, the predetermined threshold amount triggering a user alert may be about ten parts sulfate per million parts water (10 ppm of $SO_4$).

In accordance with some exemplary embodiments of the present subject matter, op-amp circuit 110 incorporates a resistor 1112 (FIG. 1A) and operational amplifier 1110 to amplify the sensed open circuit potential across the resistor 1112 from open circuit 130 between the tank 102 and the internal reference electrode 202 of sulfate sensor probe 200. In various exemplary embodiments, the op-amp 1110 may be a differential op-amp and the resistor 1112 may be a shunt resistor. The voltage sensing circuit 108 may have infinite input impedance, meaning that voltage sensing circuit 108 may draw zero current from the open circuit 130. Accordingly, one of ordinary skill in the art will recognize that the resistance of resistor 1112 can be selected to minimize or avoid current drawn from circuit 130 by voltage sensing circuit 108 to provide more accurate measurement of the open circuit potential.

As is generally known in the art, water heater 104 and/or tank 102 may include features such as ports, inlets, and other fittings for connecting, e.g. valves, thereto. Typically, such fittings are provided with internal threads. An additional fitting (not shown) may be provided for mounting the sulfate sensor probe 200 thereto. The fitting may be internally-threaded or any other known configuration suitable for attaching the probe 200.

Figure 4:
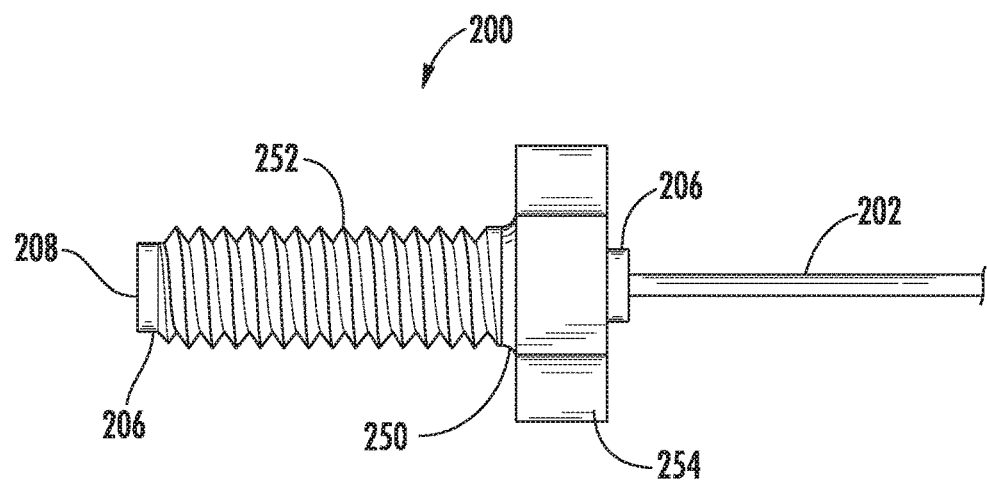
FIG. 4 provides an elevation view of a sulfate sensor probe according to an exemplary embodiment of the present subject matter.

The probe 200 includes an internal reference electrode 202 (FIG. 5) disposed within a plug 250 for mounting to tank 102. The internal reference electrode 202 is electrically insulated from tank 102, e.g., except via ion-selective membrane 208 (FIG. 4). An open circuit 130 is formed between the internal reference electrode 202 and the steel tank 102. Voltage sensor circuit 108 is connected across the open circuit 130 to sense the potential of open circuit 130. Probe 200 may include a plug 250 configured for mounting to tank 102. For example, in some exemplary embodiments, the plug 250 may comprise external threads 252 for mating with an internally-threaded fitting (not shown) on tank 102 and a head with a plurality of flats 254, e.g., forming a hexagonal or square head, for engagement with a wrench or other tool to facilitate mounting the probe 200 to tank 102. Any suitable material such as plastic or metal can be used for the plug 250, and in particular threads 252 and flats 254. In some exemplary embodiments, the threads 252 and/or flats 254 may be formed of metal, e.g., stainless steel, for compatibility with steel tank 102. For example, in embodiments wherein the plug 250 is formed of an electrically conductive material such as stainless steel, the probe 200 may further include insulating material 206 between internal reference electrode 202 and plug 250, such that the internal reference electrode 202 cannot make electric contact with the metallic plug 250 to avoid or minimize shorting out the voltage potential with the tank 102 which is in contact with the water 20 and sulfates within.

Figure 2:
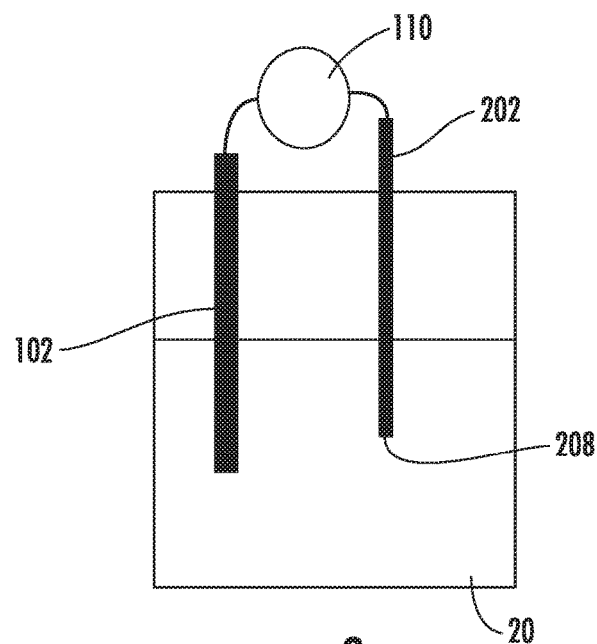
FIG. 2 provides a schematic generally representative of the components in an electrochemical sensor.

A potentiometric sensor comprising an ion-selective electrode is formed by probe 200 and tank 102. FIG. 2 provides a generalized schematic illustration of an exemplary potentiometric sensor, wherein the internal reference electrode 202 is in communication with a solution 20 only via the ion-selective membrane 208 selected for the analyte of interest, and the potentiometric sensor also includes an external reference electrode 102 in communication with the solution 20 with no ion-selective membrane therebetween. As illustrated in FIG. 2, the internal reference electrode and ion-selective membrane may be the internal reference electrode 202 and ion-selective membrane 208, respectively, of probe 200, the solution may be water 20 contained in an internal volume 22 (FIG. 3) of tank 102 and, the external reference electrode may be steel tank 102. As will be understood by those skilled in the art and as used herein, the term "water" includes solutions or mixtures containing water and, e.g., elements (such as calcium, chlorine, and fluorine), salts, bacteria, nitrates, organics, and other chemical compounds or substances. A voltage sensor, preferably a high-impedance voltage sensor such as voltage sensor circuit 110, is connected across electrodes 102 and 202 to measure the open circuit potential. The potential across the open circuit 130 is driven by sulfate ions permeating ion-selective membrane 208 of the sulfate sensor probe 200. Thus, the open circuit potential may vary proportionally with the concentration of sulfate in the water 20. In other words, the membrane 208 detects sulfates in the water 20 and translate the concentration of sulfates in the water 20 into a voltage potential. For example, the open circuit potential may range from about ninety (90) millivolts (mV) to about two-hundred thirty (230) mV, with a change of about twenty (20) to twenty-nine (29) mV per order of magnitude change in concentration of sulfate, e.g., the open circuit potential at one part sulfate per million parts water (1 ppm) may differ by about twenty (20) to twenty-nine (29) mV from the open circuit potential at ten parts sulfate per million parts water (10 ppm).

Figure 3:
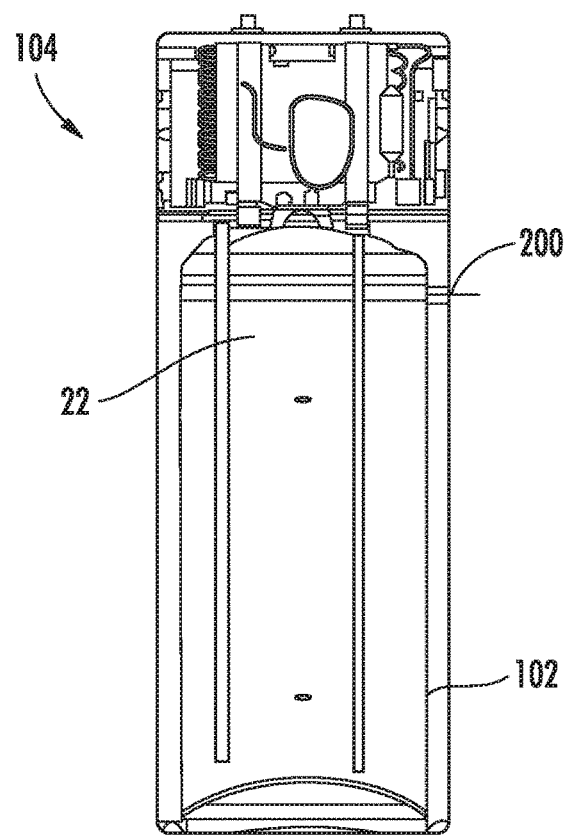
FIG. 3 provides an section view of a water heater appliance according to an exemplary embodiment of the present subject matter.

FIG. 3 provides an overview of a water heater appliance 104 which can be used with one or more embodiments of the present subject matter. The section view illustrated in FIG. 3 depicts features found in some exemplary embodiments of the water heater 104, including tank 102 and internal volume 22 defined within tank 102. Also as illustrated in FIG. 3, in some exemplary embodiments sulfate sensor probe 200 can be mounted to tank 102, e.g., by threading probe 200 into tank 102, such that the ion-selective membrane 208 of sulfate sensor probe 200 is disposed within the internal volume 22 and may be in contact with water 20 stored therein.

Figure 5:
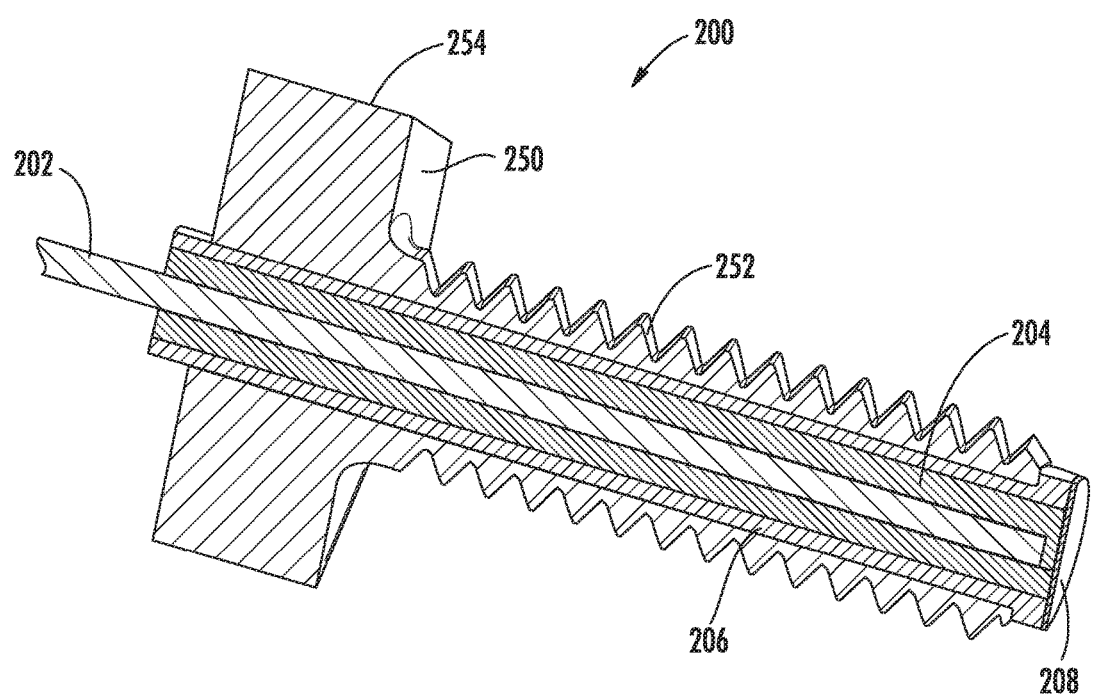
FIG. 5 provides a section view of the exemplary probe of FIG. 4.

As illustrated in FIGS. 4 and 5, the sulfate sensor probe 200 includes internal reference electrode 202 with a coating 204 enshrouding the internal reference electrode 202. In some exemplary embodiments, the coating 204 may be omitted from the tip of internal reference electrode 202 to permit direct contact between internal reference electrode 202 and membrane 208. In some exemplary embodiments, the internal reference electrode 202 may be, e.g., a copper wire or an aluminum probe. In some exemplary embodiments, the coating 204, may be, e.g., a conductive polymer, such as polyphenylene sulfide. In another non-limiting example, the coating 204 may be aluminum oxide, and in particular, in exemplary embodiments wherein the internal reference electrode 202 is an aluminum probe, an aluminum oxide coating 204 may be formed thereon by anodizing the aluminum probe. Internal reference electrode 202 and coating 204 are electrically isolated from tank 102 and water 20 by insulating material 206 except at ion-selective membrane 208 in the exemplary embodiment illustrated in FIGS. 4 and 5. The ion-selective membrane 208 may be selected for sulfate in order to detect the level of sulfate present in the water 20 within the tank 102 as discussed above in the context of FIG. 2. Because sulfate ions, which generally have a charge of negative two, permeate the ion-selective membrane, negative charge accumulates at the internal reference electrode 202 in proportion to the concentration of sulfate ions in the water 20. This accumulated charge drives the open circuit potential across tank 102 and internal reference electrode 202. Thus, the open circuit potential created varies in proportion to the concentration of sulfate in the water 20 and thereby the ion-selective membrane 208 may be used to detect the level of sulfate present in the water.

In some exemplary embodiments, for example as illustrated in FIGS. 6 & 7, internal reference electrode 202 may be provided in the form of a probe. As shown in FIG. 7, in some exemplary embodiments, the coating 204 may be omitted from a tip 210 of the internal reference electrode 202 such that tip 210 of internal reference electrode 202 is in direct contact with ion-selective membrane 208. Having internal reference electrode 202 in direct physical contact with ion-selective membrane 208 may advantageously provide enhanced electrical contact between internal reference electrode 202 and membrane 208. In particular exemplary embodiments wherein the coating 204 is an electrically insulative material, e.g., an aluminum oxide film on an anodized aluminum probe, omitting the coating 204 from tip 210 permits the selected ions that permeate ion-selective membrane 208 to interact with the probe, i.e., internal reference electrode 202, and drive an open circuit potential between internal reference electrode 202 and tank 102, as described hereinabove.

In various exemplary embodiments, regardless of whether coating 204 is an insulator, e.g., aluminum oxide, or a conductor, e.g., polyphenylene sulfide, the probe 200 may also include insulating material 206 between the internal reference electrode or probe 202 and the plug 250. The probe 202 may be, e.g., bonded to insulating material 206, or may be, e.g., mechanically joined, such as by threading. As such, in various exemplary embodiments, insulating material 206 may be epoxy, nylon, or many other polymers.

It should be understood that selecting ion-selective membrane 208 such that only sulfate ions permeate the membrane 208 is impractical because some interfering anions will likely be able to permeate the membrane 208. In accordance with exemplary aspects of the present subject matter, the ion-selective membrane 208 may be sufficiently selective to sulfate ions such that the response of probe 200 is at least one hundred (100) times more sensitive to sulfate than interfering anions. The response of probe 200 may be as much as one thousand (1,000) times more sensitive to sulfate than interfering anions. The preference of the membrane 208 for sulfate can be quantified by the matched potential method, which is recommended by the International Union of Pure and Applied Chemistry (IUPAC). According to the matched potential method, the potentiometric selectivity coefficient, $K_{A,B}$, of a membrane can be determined for an interfering ion B relative to sulfate A. Thus, ion-selective membrane 208 according to the present subject matter may have a selectivity coefficient for sulfate relative to commonly-occurring interfering anions such as carbonate, chloride and others, ranging from about one hundred to one thousand or more.

Figure 8:
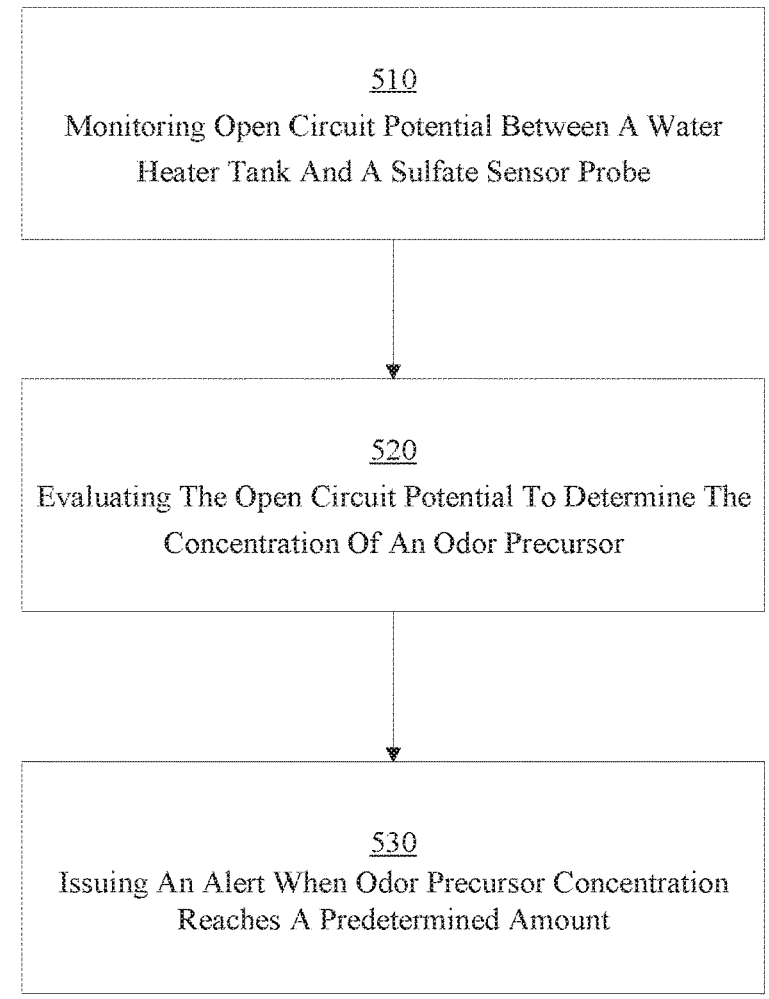
FIG. 8 provides a flow chart illustrating a method according to various embodiments of the present disclosure.

As illustrated in FIG. 8, an example method 50 of operating a water heater appliance 10 includes monitoring open circuit potential between a water heater tank and a sulfate sensor probe at step 510, evaluating the open circuit potential to determine the concentration of an odor precursor at step 520, and issuing an alert when the odor precursor concentration reaches a predetermined amount at step 530.

The sulfate-selective electrode of the present subject matter provides several advantages when used in an odor precursor detection system for a water heater appliance. For example, detection of the precursor before generation of $H_2S$ rather than the malodorous $H_2S$ compound itself permits earlier detection of a potential problem before an actual odor and/or taste problem develops. Thus, the user can be alerted to the potential problem and take proactive steps, such as filtering out the sulfates, reducing the galvanic current running from the anode to tank wall (cathode), and/or sanitizing the tank to eliminate sulfate reducing bacteria in the tank, to prevent or minimize generation of $H_2S$ in the water heater. As another example advantage, the probe 200 can be mounted to the tank 102 using a standard-type fitting for relative ease of manufacture and installation. As yet another example of the several advantages, the probe 200 is operable under a variety of thermochemical conditions, including those commonly found in water heater appliances.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A water heater odor precursor detection system, comprising:

a water heater tank;

a sulfate sensor probe mounted to the water heater tank, the sulfate sensor probe comprising an internal reference electrode, the internal reference electrode separated from the water heater tank by an ion-selective membrane, the ion-selective membrane selected for sulfate ions, and the sulfate sensor probe further comprising a conductive polymer between the ion-selective membrane and the internal reference electrode;

a voltage sensor circuit in operative communication with the water heater tank and the sulfate sensor probe, the voltage sensor circuit operable to sense an open circuit potential between the water heater tank and the sulfate sensor probe;

a controller configured to receive a signal from the voltage sensor circuit, the signal indicative of the sensed open circuit potential, and the controller configured to provide an output signal based on the signal; and an indicator configured to provide an indication of odor precursor detection based on said output signal.

2. The system of claim 1, wherein the voltage sensor circuit comprises a differential operational amplifier and a shunt resistor coupled across differential inputs of the differential operational amplifier.

3. The system of claim 2, wherein the shunt resistor is connected at one end to an internal reference electrode of the sulfate sensor probe and at the other end to the water heater tank.

4. The system of claim 1, wherein the water heater tank defines an interior volume and the ion-selective membrane of the probe is disposed within the interior volume of the tank.

5. The system of claim 1, wherein the water heater tank comprises a threaded port and the sulfate sensor probe has mating threads for mounting to the threaded port of the water heater tank.

6. The system of claim 1, wherein said indicator comprises one or more of a visual, audible, and electronic device.

7. The system of claim 1, wherein said indicator comprises one or more of a light emitting diode (LED) and a sound source.

8. The system of claim 1, wherein said indicator comprises a network-enabled device operable to send indications of odor precursor detection to a remote location.

9. A method of alerting a consumer upon detection of an odor precursor in a water heater, the method comprising:

monitoring open circuit potential between a water heater tank and an internal reference electrode of a sulfate sensor probe, the internal reference electrode separated from the water heater tank by an ion-selective membrane selected for sulfate ions and the sulfate sensor probe further comprising a conductive polymer between the ion-selective membrane and the internal reference electrode, the open circuit potential driven by sulfate ions permeating the ion-selective membrane of the sulfate sensor probe;

evaluating the open circuit potential to determine a concentration of sulfate; and issuing an alert when the concentration of sulfate reaches a predetermined amount.

10. The method of claim 9, wherein monitoring open circuit potential comprises monitoring the output of a differential operational amplifier whose inputs are coupled to a shunt resistor, the shunt resistor connected across the open circuit.

11. The method of claim 9, wherein issuing an alert comprises one or more of issuing a visual, audible, and electronic alert.

12. The method of claim 9, wherein issuing an alert comprises issuing an electronic alert, the electronic alert comprising one or more of activating a light emitting diode (LED) and a sound source.

13. The method of claim 9, wherein issuing an alert comprises issuing an electronic alert through a network-enabled device to a remote location.

14. The method of claim 9, wherein the predetermined amount is about ten parts odor precursor per million parts water.

* * * * *